(12) United States Patent
Jud et al.

(10) Patent No.: US 6,908,476 B2
(45) Date of Patent: Jun. 21, 2005

(54) MICRO SURGICAL CUTTING INSTRUMENT CONFIGURED AS SCISSORS

(75) Inventors: Oliver Jud, Löhningen (CH); Werner Maag, Glarus (CH)

(73) Assignee: Alcon Grieshaber AG, Schaffhausen (CH)

( * ) Notice: Subject to any disclaimer, the term of this patent is extended or adjusted under 35 U.S.C. 154(b) by 240 days.

(21) Appl. No.: 10/032,306

(22) Filed: Dec. 21, 2001

(65) Prior Publication Data
US 2003/0120305 A1 Jun. 26, 2003

(51) Int. Cl.$^7$ .............................................. A61B 17/00
(52) U.S. Cl. ....................... 606/205; 606/174; 606/107
(58) Field of Search ................................ 606/174, 205, 606/206

(56) References Cited

U.S. PATENT DOCUMENTS

| | | | | | |
|---|---|---|---|---|---|
| 4,027,510 | A | * | 6/1977 | Hiltebrandt | 72/37 |
| 4,108,211 | A | * | 8/1978 | Tanaka | 138/120 |
| 4,433,687 | A | * | 2/1984 | Burke et al. | 606/180 |
| 5,047,008 | A | * | 9/1991 | de Juan et al. | 604/22 |
| 5,249,121 | A | * | 9/1993 | Baum et al. | 606/1 |
| 5,439,000 | A | * | 8/1995 | Gunderson et al. | 600/473 |
| 5,486,185 | A | * | 1/1996 | Freitas et al. | 606/142 |
| 5,498,256 | A | * | 3/1996 | Furnish | 606/1 |
| 5,810,877 | A | * | 9/1998 | Roth et al. | 606/205 |
| 5,928,263 | A | * | 7/1999 | Hoogeboom | 606/205 |
| 6,051,011 | A | * | 4/2000 | Weidenbenner | 606/171 |
| 6,066,102 | A | * | 5/2000 | Townsend et al. | 600/564 |
| 6,419,688 | B1 | * | 7/2002 | Bacher et al. | 606/205 |

* cited by examiner

Primary Examiner—Julian W. Woo
Assistant Examiner—Bradford C Pantuck
(74) Attorney, Agent, or Firm—Henry M. Feiereisen; Ursula B. Day

(57) ABSTRACT

A cutting instrument configured as scissors has a housing formed as a handle with a functional unit disposed therein; supported in the functional unit is a probe configured as a hollow needle which co-axially supports a rod projecting from the probe in axial direction and which comprises at its distal end a cutting device and wherein the cutting device has two cutting members provided with cutting blades that can be configured in an arc-shape or a straight shape, wherein from an open position the cutting blades correspond to each other at an acute angle, they are brought into engagement with each other to a closed position for a cutting action by means of a sliding movement of the probe relative to the scissors tip.

24 Claims, 6 Drawing Sheets

MICRO SURGICAL CUTTING INSTRUMENT CONFIGURED AS SCISSORS

BACKGROUND OF THE INVENTION

The invention relates to a micro-surgical cutting instrument of the type configured as scissors, which includes a housing formed as a handle, and a device disposed in the housing for an axial sliding movement of a probe, that is configured as a hollow needle and which axially supports a rod with the cutting device disposed at the distal end of the rod.

The present invention is generally directed to surgical procedures and special problems that occur when such procedures are carried out in body cavities of a living being. For example, certain difficulties occur when treating the eye of a living being for retinal diseases. Such diseases oftentimes appear in conjunction with hypertonia or vascular changes. In the course of such diseases, venous branch occlusions (phlebemphraxis) can occur in an area where veins and arteries cross each other and are surrounded by a substantially transparent skin sheath or membrane, whereby the artery which overlays the vein can press on the vein in such a way that the vein becomes pinched. By separating (cutting) and removal of the skin sheath, such venous branch occlusions can be eliminated or can even be prevented.

When carrying out microsurgical procedures of, for example the afore-described type, in addition to a steady hand when handling the instrument, precise functioning of the instrument used for this purpose is required. Thus, it is particularly important for this purpose that the instrument is designed, so the diseased tissue can easily be reached and grasped with the instrument and that the instrument can be held steady in the surgeon's hand over a along period of time and that the instrument's cutting position can be visually easily recognized.

The generally known prior art instruments have certain drawbacks such as, for example, they can damage the tissue due to improper configuration of the instrument's cutting blades; or, even prior to cutting the tissue, the blades can deform the tissue in a manner rendering it unsuitable for the cutting action, or the cutting blades unexpectedly retract during the procedure. In many ways these known cutting instrument no longer fulfill the requirements of modern microsurgery and are not suited for surgery on delicate tissue structures, in particular for surgery on the delicate tissue of the retina.

It would thus be desirable and advantageous to provide an improved surgical instrument which overcomes the above-described shortcomings.

SUMMARY OF THE INVENTION

According to one of many aspects of the present invention, an improved cutting instrument is provided, which is designed to obviate the afore-stated shortcomings and which is so configured that microsurgical procedures are made easier and can be carried out even on delicate tissue, and especially also on retinal tissue which procedures must be carried out in a small space under precise cutting conditions that are gentle to the tissue The cutting instrument according to the invention comprises two axially oriented cutting members which are projecting at a distal end from a tube-shaped probe. Each of the cutting members is provided with a cutting blade and are either outwardly bent at an angle or are straight-shaped. The cutting blades are provided with cutting edges facing each other at an acute angle along a distance extending from each of the blade tips of the cutting blades in the direction of the probe when the scissors is in an open position. Due to a movement of the probe relative to the cutting blades in the direction towards the tip of the scissors the two cutting edges are brought into engagement with each other for a cutting action.

In accordance with the invention, precise surgical procedures, without damage to the tissue when treating venous branch occlusions are realized with the cutting instrument. Use of the cutting instrument according to the invention is particularly advantageous for surgical procedures on the retina, for example for sub-retinal surgery.

In a further embodiment of the cutting instrument according to the invention, the instrument is provided with a light guide, which is axially disposed in the tube-shaped probe and connected at one end to a light source and at the other end is configured for illuminating the distal end of the cutting instrument specifically the two cutting blades that are projecting from the probe and facing each other in an open position or in closed position. The light guide is designed to illuminate the tip of the scissors, respectively the blade tips of the two cutting members during the surgical procedure, thereby illuminating the surgical field and rendering the tissue in the immediate area well visible.

For optimal handling of the instrument according to the invention, an optical channel provided with an optical guide is associated with the light guide in the probe. By means of this optical guide, images from the surgical field and the viewing field are transmitted to a monitor screen from initial insertion of the probe and for the duration of the surgical procedure. This particular embodiment of the instrument provides a good visualization of the surgical field making it easily visible for the operating surgeon so that exact surgical procedures in small organ cavities can be realized.

It is pointed out that the cutting instrument according to the invention is not limited to the field of ophthalmology and that the cutting instrument, without any modifications, can be used for a variety of surgical procedures in the body cavities of a living being. Without deviating from the basic idea of the invention, further modifications and embodiments of the cutting instrument and each of its functional elements is possible.

BRIEF DESCRIPTION OF THE DRAWINGS

The above and other aspects, features and advantages of the present invention will now be described in more detail with reference to the accompanying drawing in which.

DETAILED DESCRIPTION OF THE PREFERRED EMBODIMENTS

Throughout all the FIGURES, same or corresponding elements are generally indicated by same reference numerals.

Figures 1, 2:
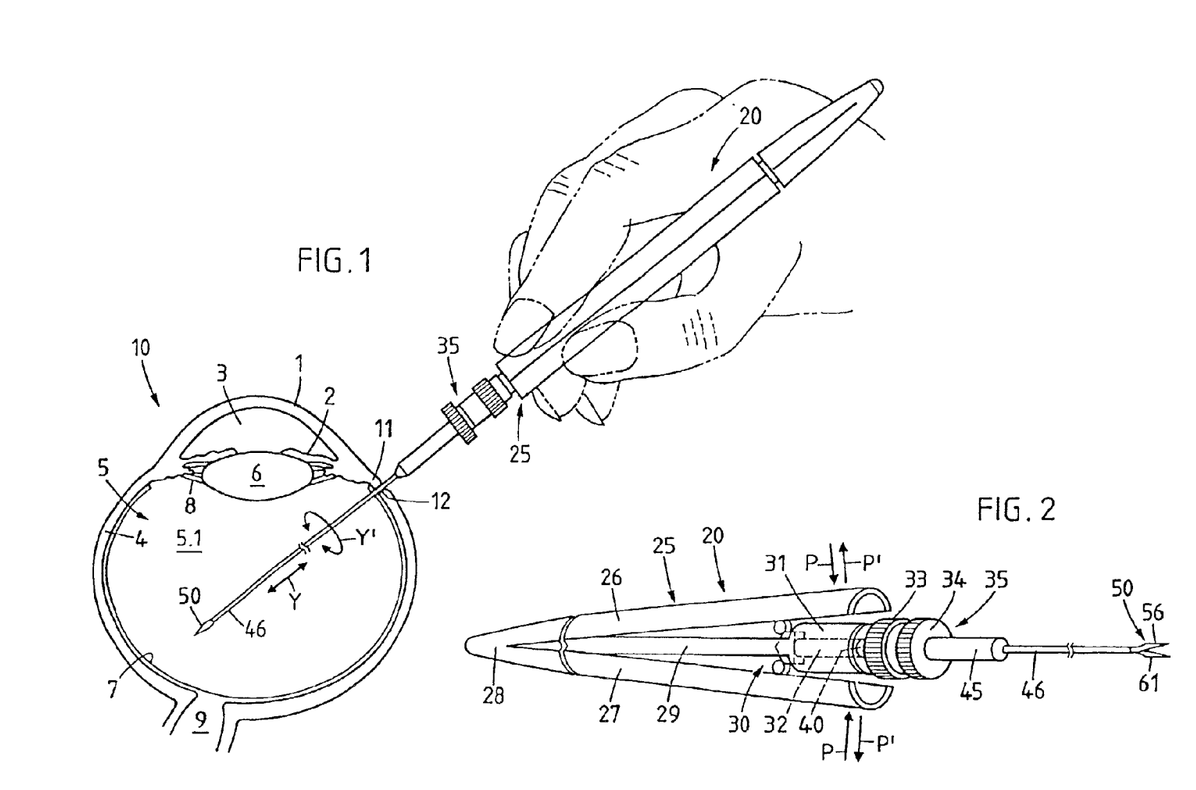
FIG. 1 is a schematic illustration of an eye showing the probe of a cutting instrument inserted into the vitreous humor.
FIG. 2 is an approximate perspective view of a first embodiment of a cutting instrument with the functional unit disposed therein for a cutting device having two blades.

Turning now to FIG. 1, there is shown the horizontal section of an eye 10 on an enlarged scale, showing the cornea 1, the iris 2 with the pupilla 3, the sclera 4, and the vitreous humor 5 with the vitreous humor cavity 5.1 and lens 6, the retina 7 and the zonula fibers 8. The optic nerve bundle 9 (opticus), which projects from the eye, is schematically represented in the area of the eye background.

Further shown in FIG. 1 in schematic representation, is the cutting instrument 20, which is inserted into the space of the vitreous humor 5.1 of the eye by means of the probe 46, which is disposed on the instrument 20. The cutting instrument 20 comprises essentially a housing 25 which is operatively connected with a sliding unit not shown in detail in FIG. 1 and a functional unit 35 connected to probe 46, which is configured as a hollow needle. Disposed at the distal end of probe 46 is the cutting device 50, which, in FIG. 1, is shown in schematic representation.

When carrying out the surgical procedures, the ophthalmologist or surgeon cuts an incision 12 into sclera 4 in the area of the pars plana 11, through which the probe 46 is inserted into the vitreous humor 5.1. After removing the probe 46 together with the cutting device, incision 12 closes up by itself.

As schematically shown in FIG. 1, the cutting instrument 20 with the probe 46 and the cutting device 50 can be moved relative to the inner side of the retina which it faces within the vitreous humor 5.1 in axial direction of double arrow Y, and also rotated about the longitudinal axis (not shown) according to the direction of arrow Y'.

The probe 46, which is configured as a hollow needle for insertion into the vitreous humor 5.1 has an outer diameter in the range of about 1.0 mm and an inner diameter of about 0.8 mm. An axially oriented rod 47, which is disposed In the tube-shaped probe 46 projecting from probe 46 at a distal end, is provided with a cutting device 50. The cutting device 50 is designed and configured especially for cutting delicate tissue and structures. The cutting device 50 comprises two corresponding cutting blades for engagement with each other in a cutting action. Other features and embodiments of the device are further discussed herein.

A preferred embodiment is depicted in a schematic representation in FIG. 2 and shows an approximate three-dimensional view of the cutting instrument 20 with the cutting device 50 configured for the cutting of delicate retinal structures. The cutting instrument 20 comprises a housing 25 comprised of two semi-circular shaped elongated housing parts 26 and 27 that are formed as a handle. At their distal end, the two housing parts 26 and 27 are connected to each other by means of a cap closure 28 not shown here in further detail. A carrying arm 29 is disposed between the two housing parts 26 and 27, which are in operative engagement with a sliding device 30. Disposed at the proximal end of the carrying arm 30 is a guide piece 31 provided with a threaded attachment to a functional unit, generally referred with reference numeral 35.

An axially oriented pin 32 is supported in the cylindrical guide piece 31 as schematically illustrated in FIG. 2 and the guide piece 31 is operatively connected at one end with the sliding mechanism 30 and at the other end with the approximately pin-shaped control member 40. The control member 40 is supported in the functional unit 35 for an axial sliding motion.

The functional unit 35 is connected to the carrying arm 29 of the cylindrical guide piece 31 by means of the swivel nut 33 in such a manner that the pin-shaped control member 40 is in operative engagement with the pin 32 of sliding mechanism 30. The functional unit 35 is further described in detail with reference to FIGS. 3 and 4.

The cutting instrument 20 shown in the embodiment in FIG. 2 is brought into a functional mode by means of applying manual pressure on the two housing parts 26, 27 according to double arrow P, whereby the sliding mechanism 30 is activated. The pin 32, which is supported in guide piece 31 is moved jointly with the control member 40, which is operatively connected with the guide piece 31, and slides in axial direction, whereby the cutting device 50 which acts jointly with the probe 46 is actuated. When reducing, or respectively eliminating the manual pressure from the two housing parts 26 and 27, they are moved back according to double arrow P' due to the restoring force of a compression spring disposed at the functional unit 35 and operatively connected to the control member 40 and the pin 32.

Figure 3:
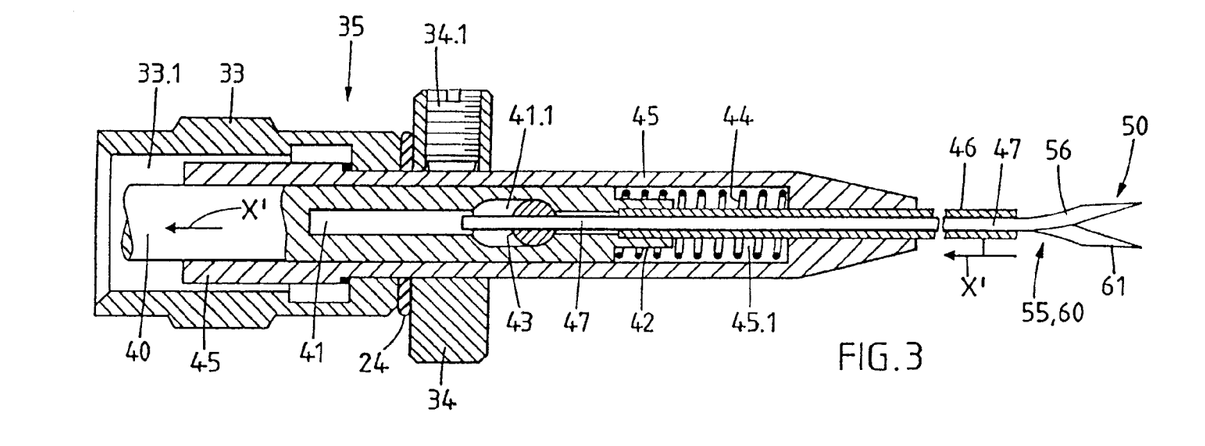
FIG. 3 is a section view of the functional unit on an enlarged scale with the cutting members disposed at the elongated rod and in open position.

FIG. 3, shows a section of the functional unit on an enlarged scale, wherein the swivel screw 33 has a recess 33.1 with a guide sleeve 45 supported therein and an intermediary ring 24 disposed at the outer circumference of the swivel screw 33 and a control ring 34. Control ring 34 is attached to the guide sleeve 45 by means of screwed-in threaded pin 34.1. The control member 40 is disposed in a cylindrical recess 45.1 of the guide sleeve 45. The end of the control member, which is supported in recess 45.1 of the guide sleeve 45, is provided with a cylindrical piece 42 which is configured in a set-off manner. A compression spring 44 is supported at one end by the cylindrical piece 42 and with the other end bears against the inner wall of the guide sleeve 45. The parts 33, 24, 34, 45 and 40 of the functional unit jointly comprise a unit.

As is further depicted in FIG. 3, the control member 40 is provided with an axial blind bore 41 and a recess 41.1-oriented perpendicular thereto. The blind bore 41 is configured for receiving and supporting rod 47 and for receiving the probe 46 which is configured as a hollow needle and attached to the control member 40. The rod 47 that is supported in the tube-shaped probe 46 is provided with a cutting device 50 at its distal. The cutting device 50 comprises essentially two cutting members 55 and 60 projecting in axial direction from the distal end of probe 46 and has scissor-like cutting blades 56 and 61 for a corresponding engagement with each other during cutting action.

The tube-shaped probe 46 is operatively connected with the axially slidable control member 40, for example by means of a glue-, weld- or solder-connection in a manner not shown here in further detail. The end of the rod 47, supported in probe 46, is secured against axial displacement by means of at least one threaded pin 43. At the distal end of rod 47, which projects from the probe 46, the cutting device 50 for cutting delicate tissue structures is disposed. Shown In FIG. 3 are the two cutting blades 56 and 61, which are in substantially open position due to the retraction of probe 46 along the direction of arrow X' and the spring elastic restoring force of the cutting blades 55 and 60.

Figure 4:
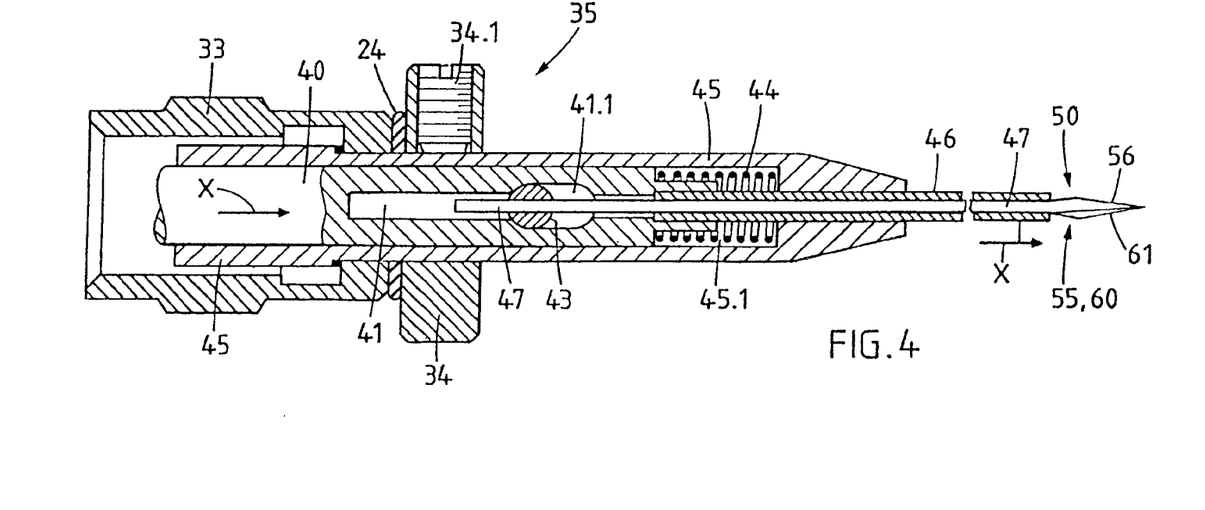
FIG. 4 shows the functional unit according to FIG. 3 with the cutting members disposed at the rod and in a closed position.

FIG. 4 shows the functional unit 35 and its parts described in FIG. 3. In a variation from FIG. 3, the control member 40 in FIG. 4 is axially moved according to arrow X against the restoring force of the compression spring 44 relative to the rod 47, which is secured by means of threaded pin 43 with the guide sleeve 45. During this movement, the two cutting blades 56 and 61 are brought into a closed position when the probe 46 is moved in a sliding motion onto the two elongated cutting members 55 and 60. The movement of the tube-shaped probe 46 in axial direction relative to the cutting device 50 is realized by means of the manually actuated cutting instrument 20 as in embodiment shown in FIG. 2.

Figures 5, 6A, 6B, 7A, 7B, 8:
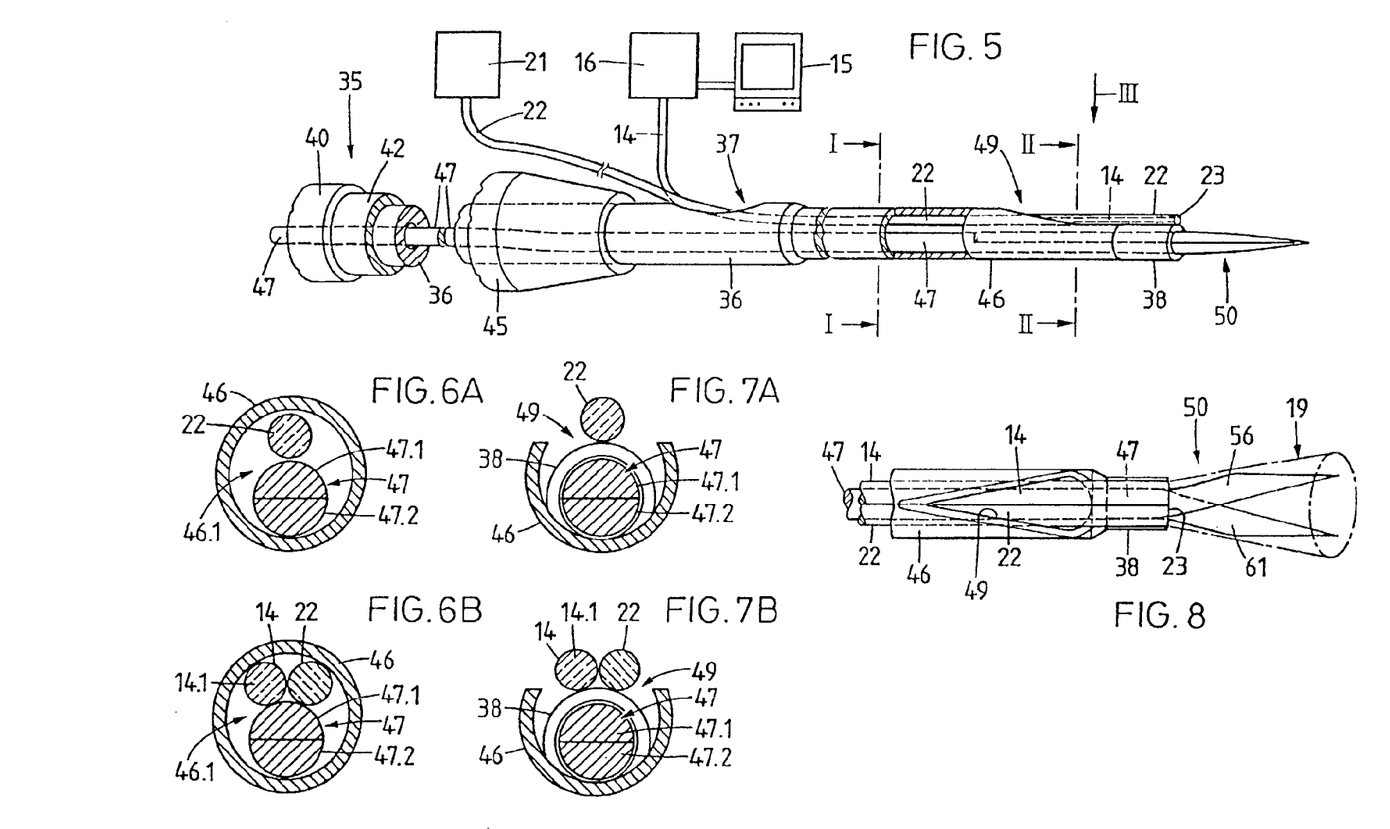
FIG. 5 is a partial view of a second embodiment of the functional unit with the rod disposed in the tube-shaped probe and the associated light guide and/or the associated optical channel.
FIG. 6A is a cross sectional view of a variation of the probe viewed along the line I—I in FIG. 5 showing the rod disposed therein and the associated light guide.
FIG. 6B is a cross sectional view of a second variation of the probe viewed from the line I—I showing the rod disposed therein and the light guide and the optical channel associated therewith.
FIG. 7A is a cross sectional view of the first variation of the probe according to FIG. 5 viewed along line II—II showing the rod and the associated light guide.
FIG. 7B is a cross sectional view of the second variation of the probe according to FIG. 5 viewed along line II—II showing the rod and the associated light guide and optical channel.
FIG. 8 is a top view according to the arrow III of FIG. 5 of the front portion of the cutting instrument with the associated light guide.

FIG. 5 shows a side view of a further embodiment and a section of a portion of the functional unit 35, which is configured substantially similar to a functional unit 35 as seen in FIGS. 3 and 4. In a variation of the guide sleeve 45 as seen in FIGS. 3 and 4, FIG. 5 shows a first tubular piece 38, which is supported in guide sleeve 45 and which is connected at one end to the control member 40 in a manner not shown here in detail. The tube-shaped probe 46 is co-axially disposed and connected at the other end of the first tubular piece 36. A second tubular piece 36 is eccentrically disposed in and connected to the front end of the tube-shaped probe 46.

As is further shown in FIG. 5, the axially oriented rod 47 provided at its front end with the cutting device 50, is co-axially disposed in the frontward second tubular piece 38. A portion further along and adjacent to the front end of the rod 47 the rod 47 is disposed in a slightly eccentric oriented manner in the tube-shaped probe 46 and the first tubular piece 36 connected thereto. The other end of the rod 47, as shown in FIGS. 3 and 4, is disposed in the blind recess 41 of control member 40 and secured against axial displacement by means of the screwed in threaded pin 43. The first tubular piece 36 which is supported in the guide sleeve 45 and probe 46 and the second tubular piece 38, jointly form a structural unit with the control member 40 and is slidably movable in axial direction relative to the fixed rod 47 and the cutting device 50.

In that embodiment, the first tubular piece 36 has an inlet opening 37 for insertion of a light guide 22. Light guide 22 is introduced through the inlet opening 37 into the first tubular piece 36 and from there is inserted into the probe 46. The light guide 22 penetrates the tube-shaped probe 46 in axial direction and projects from the end thereof through an outlet opening 49. The light guide 22 projecting from the probe 46 is preferably attached at the outer wall of the second tubular piece 38 by means not shown here in detail. The distal area of the two cutting blades 56 and 61 is illuminated by means of a light cone 19 which emerges from the front face 23 of the light guide 22, as shown in schematic representation in FIG. 8. The light guide 22 stands in operative connection with the light source 21 as schematically represented in FIG. 5. For example, a battery which is disposed in housing 25 of instrument 20 (FIG. 2) can serve as a light source.

In a further variation of the embodiment as shown in FIG. 5, an optical channel 14, as for example known in the prior art is arranged in tube-shaped probe 46. For the purpose of transmitting images, e.g. monoscopic images, the optical guide 14.1 is disposed within the optical channel 14. The optical guide 14.1 which is disposed in optical channel 14 is operatively connected to a camera 16 schematically shown in FIG. 5, via a line 14, which projects through the inlet opening 37 of probe 46 and the camera is connected to a monitor screen 15. When the distal end of the optical guide 14.1 is pointed to the surgical field, images from the surgical area are recorded with the camera 16 and transmitted for viewing the surgical procedure via a monitor screen 15. The known optical guide 14.1 comprises for example one or more bundles of optical fibers. In another variation, the optical guide 14.1 is integrated into the line 14 and extends axially to the distal end of the probe 46.

FIG. 6A shows a section of a first variation of the tube-shaped probe 46 along line I—I in FIG. 5 on an enlarged scale, wherein the rod 47 is disposed in the interior space 46.1 of probe 46 and the semi-circular arms 47.1 and 47.2 are shown in a profile section as well as the light guide 22.

FIG. 6B shows a section along to line I—I in FIG. 5 of a second variation, with the tube-shaped probe 46 shown on an enlarged scale and disposed in the inner space thereof and rod 47 with the two semi-circular arms 47.1 and 47.2. Differing from the variation as seen in FIG. 6A, this variation has in addition to the light guide 22, an optical channel 14 supporting an optical guide 14' axially disposed within the probe 46.

FIG. 7A shows in a first variation a section of the probe 46 seen along the line II—II of FIG. 5 on an enlarged scale and the outlet opening 49 shown in that portion. The second tubular piece 38 is disposed on probe 46 and the rod 47 which is co-axially supported within the second tubular piece 38 is configured with the two semi-circular shaped arms 47.1 and 47.2. The light guide 22 is bearing against the outer wall of the second tubular piece 38 which projects from the recess 49 and is attached thereto by means not further shown here in detail.

FIG. 7B shows a second variation of a section of the probe 46 seen along the line II—II of FIG. 5 on an enlarged scale with the second tubular piece 38 disposed thereon and the rod 47 co-axially supported therein. Differing from the variation as seen in FIG. 7A, this embodiment has in addition to the light guide 22, also the optical channel 14 and the optical guide 14.1 associated therewith. The elements 22 and 14 which project from recess 49 are attached adjacent to the outer wall of the second tubular piece 38 by means shown here in detail.

FIG. 8 is a top view in accordance with the direction of arrow III on an enlarged scale showing a portion of the probe 46 with the second tubular piece 38 and the outlet opening 49 oriented in axial direction. The light guide 22 is seen as projecting from the exit opening 49 and the associated optical channel 14 and are both bearing against the second tubular piece 38. The cutting device 50 with the two blades 56 and 61 projecting from the second tubular piece 38 are in open position.

The light guide 22 is at its front side 23 configured preferably in a manner such that the light rays forming the light cone 19 are emitted at a limited spatial angle, preferably directed to the distal end of the cutting device 50 so that the surgeon has a good view of the cutting function during the surgical procedure.

In a further preferred embodiment, the light guide 22 is associated with the optical channel 14 which houses optical guide 14.1 in such a manner, that the images from the surgical field and the observation field can both be transmitted to the monitor screen 15 during the surgical procedure where it can be viewed by the surgeon.

FIGS. 9A to 9F shows the first variation of the cutting device 50. The cutting device depicted in FIG. 9A as a side view, comprises the tubular probe 46 with the rod 47 which is configured having a circular cross sectional profile and the two cutting members 55 and 60 are disposed at the rod 47. The two elongated cutting members are configured upwardly bent at their front-end area. The second cutting member 60, which has a semicircular shape, is preferably configured as an integral extension from the rod 47. The front end of the first cutting member 55 which also has a semicircular profiled cross section is connected to the rod 47 or respectively to the second cutting member by means of a glue-, weld- or solder connection joined at points 48, 48.1 and 48.2.

The two opposite axially extending connection points 48.1 and 48.2 (FIG. 9A) have a length of about 5 mm, so that the two cutting members 55 and 60 can be spread apart in the front area against their spring-elastic restoring force. In the front area, the two cutting members 55 and 60 are disposed each with an integrally formed elongated cutting blade. The cutting blades 56 and 61 separated from each other by a gap 59, are in the shape of an arc with a relatively large radius (FIG. 9F) and are spread relative to each other for pretensioning. In the position according to FIG. 9A, the cutting blades 56, 61 with the integrally formed tops 58 and 63 are crossing each other at the front area at a closing angle γ', approximately in the range from 1°–3°, in the preferred embodiment the angle γ' is 1.4°.

Figure 9A:
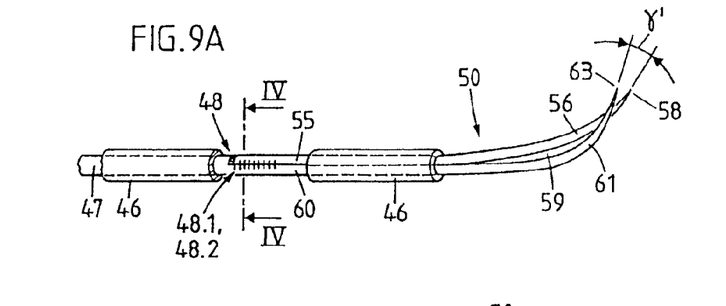
FIG. 9A is an approximate side view of the first variant of the cutting instrument with the blade members shown in an approximate open position.
Figure 9B:
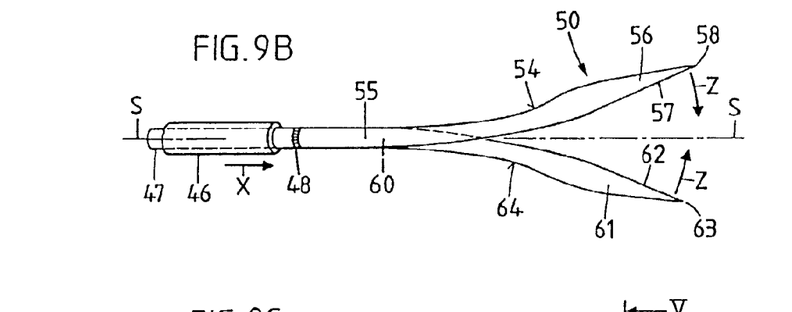
FIG. 9B is a top view of the cutting device according to FIG. 9A with the two blade members spread apart relative to one another.

In FIG. 9B, the cutting device 50 is shown in a top view with the tube-shaped probe 46 and the rod 47 disposed therein, the two cutting members 55 and 60 and the integrally formed cutting blades 56 and 61. In this position, the two corresponding cutting blades 56 and 61 with cutting edges 57, 62 and the cutting blade tips 58, 63, are spread apart at a distance from each other relative to the longitudinal axis S—S. The outer horizontal sides 54 and 64 of the two cutting members 55 and 60 are arc-shaped and so configured that when the probe 46 is moved in axial direction according to arrow X, the two cutting blades 56 and 61 are moving against the spring elastic restoring force according to arrow Z in a synchronous motion in the direction of the longitudinal axis S—S.

Figure 9C:
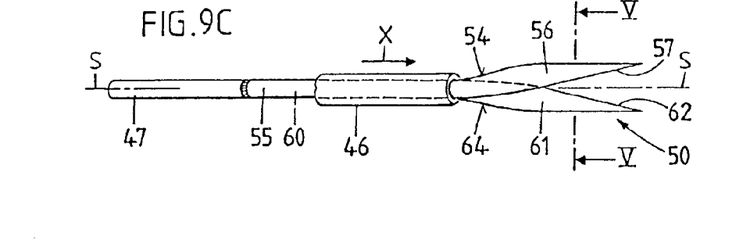
FIG. 9C is a partial view of the cutting device according to FIG. 9B with the blade members shown in substantially open position.

FIG. 9C shows the cutting device 50 in accordance with FIG. 9B and when sliding the probe 46 in axial direction according to arrow X the two cutting members 55 and 60 with the integrally formed cutting blades 56 and 61 are partially in closed position, whereby the cutting edges are in engagement with each other for a cutting action.

Figure 9D:
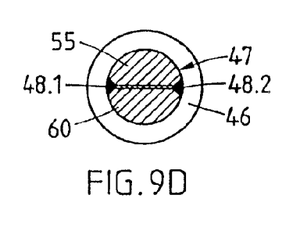
FIG. 9D is a section view of the rod disposed within the probe of the cutting device viewed along the line IV—IV according to FIG. 9A.

FIG. 9D shows a profiled section of the semi circular configured cutting members 55 and 60 of rod 47 in accordance with the line IV—IV of FIG. 9A and the tube-shaped probe 46. The cutting blades 55 and 60 that are facing each other with their flat sides are joined together at point 48 as described in connection with FIG. 9A, as well as at the opposite sides 48.1 and 48.2.

Figure 9E:
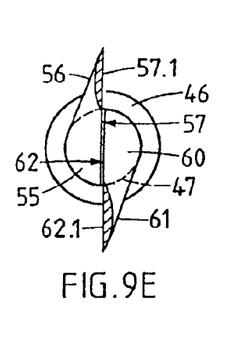
FIG. 9E is a section view of the probe with the two blade members in open position viewed along the line V—V of FIG. 9C.

FIG. 9E shows a section in accordance with the line V—V in FIG. 9C, with the probe 46 and the rod 47 disposed therein and the cutting members 55, 60 provided with the cutting blades 56 and 61 and the cutting edges 57 and 61 with the cutting surfaces 57.1 and 62.1 facing each other.

Figure 9F:
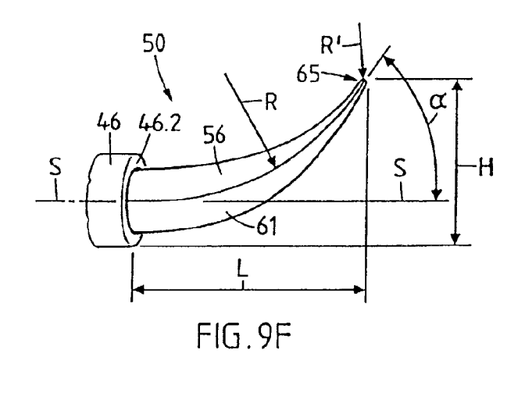
FIG. 9F is a side view on an enlarged scale of the distal end of the scissors in closed position.

FIG. 9F shows the distal end of the cutting device 50 on an enlarged scale according to the first variation with the two cutting blades 56 and 61 which taper towards the rounded tip of the scissors 65. The tip of the scissors 65 is preferably rounded at a radius R' in the range of from 0.01 mm to 0.03 mm and can be utilized for pricking the tissue. The two cutting blades 56 and 61 are configured as elongated axially extending cutting device 50 with the two cutting blades 56 and 61 in jointly bent configuration or respectively offset relative to the longitudinal axis S—S, at an acute offset angle α and a radius R.

In FIG. 9F, the cutting device 50 is shown in closed position and the two cutting blades 56 and 61 have a length L extending from the front side 46.2 of probe 46 to the tip of the scissors 65, which is greater than the height H extending from the outer diameter of the probe 46 to the tip of the scissors 65. According to the first variation, the portion of the cutting device 50 projecting from the probe 46 is relatively elongated and has an arc shaped configuration at a distance to the front side 46.2 of probe 46 with a bending angle α and radius R relative to the longitudinal axis S—S. In the embodiment as shown, the length L is about 2.5 mm to 3.8 mm and the height H is about 1.7 mm to 2.0 mm. The radius R is about 1.8 mm to 2.0 mm and the bending angle α is in the range of about 40° and 65°. In a preferred embodiment the bending angle α is in the range between 55° and 60°.

Figures 10A, 10B, 10C, 11A, 11B, 14:
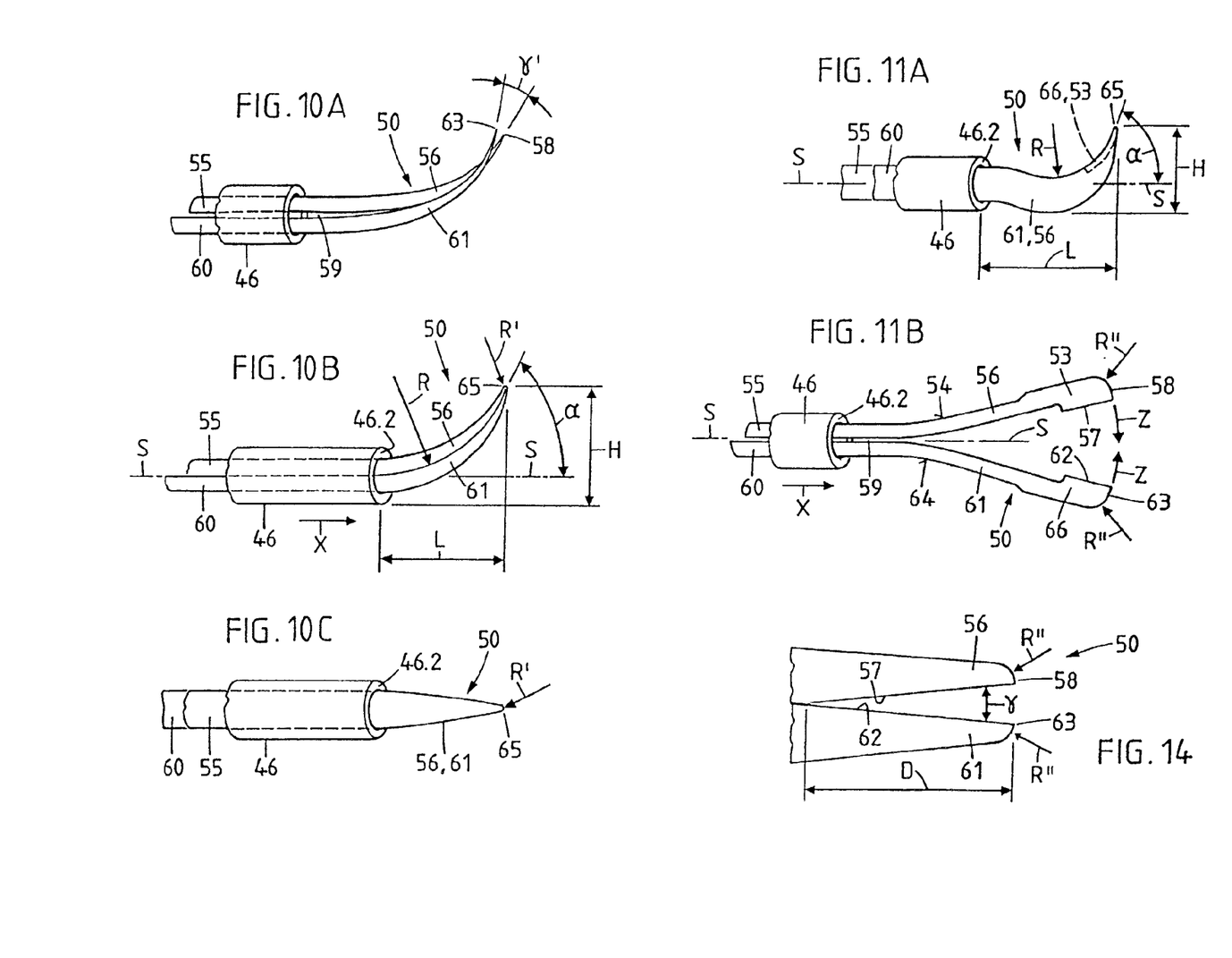
FIG. 10A is a side view of the second variation of the cutting device with the two blade members in an open position.
FIG. 10B is a side view of the cutting device according to FIG. 10A with the two blade members in closed position.
FIG. 10C is a top view of the cutting device according to FIG. 10B.
FIG. 11A is a side view of a third variation of the cutting device.
FIG. 11B is a top view of the cutting device according to FIG. 11A with the blade members shown in a spread-apart position.
FIG. 14 is a top view on an enlarged scale of the distal end of the two blade members approximately in a cutting position for the respective cutting devices.

In FIGS. 10A to 10C, a second variation of the cutting device is shown, which is essentially similar to the that of the first variation and which comprises the tube-shaped probe 46, and the two cutting members 55 and 60 with the integrally formed cutting blades 56 and 61 disposed thereon. The position of the probe as shown in FIG. 10A is such that the spring elastic restoring force between the two cutting members 55 and 60, results in the gap 59 and the blade tips 58 and 63 correspond to each other in an approximately open position. By means of a sliding motion in axial direction of the tube-shaped probe 46 relative to the two cutting members 55 and 60, the cutting blades 56 and 61 are moving against the spring elastic restoring force into a closing position for the cutting action. In this position according to the FIG. 10A, the cutting blades 56, 61 with the integrally formed tips 58, 63 which are crossing each other at the tip area at a closing angle γ' at a range from 1° to 3°, with the preferred embodiment having a closing angle γ' of 1.4°.

FIG. 10B shows the cutting device 50 with the probe 46 and the two cutting members 55, 60 disposed therein in accordance with FIG. 10A, where due to the axial sliding motion of the tube-shaped probe 46, the two cutting blades 56 and 61 that are tapering towards the tip of the scissors 65 in the direction of arrow X, are in a closed position.

Differing from the first variation in accordance with FIG. 9F, in the second variation according to FIG. 10B, the length L, which extends from the front side 46.2 of the probe 46 to the tip of the scissors 65 with respect to the height H, which extends from the outer diameter of the probe 46 to the tip of the scissors 65, is approximately the same. The radius R is preferably smaller than the length L. Here, the portion of the cutting device 50 projecting from the probe 46 is has a shorter configuration than in FIG. 9F and, relative to the longitudinal axis S—S directly bent with a radius R at the front side 46.2 of the probe 46. In the second variation in accordance with FIG. 10B, the length L and the height H are about 1.7 mm to 2.0 mm. The radius of the two arcuate cutting blades 56. 61 relative to the longitudinal axis S—S in the direction of the tip of the scissors 65 is at an angle α in the range of about 60° to 70° preferably at an angle α of 65° and jointly bent.

FIG. 10C shows a top view of the second variation of the cutting device 50 with the tube-shaped probe 46 and the two cutting members 55 and 60 and the crossed cutting blades projecting at the front side. The cutting blades 56 and 61, starting from the front side 46.2 of probe 46 are tapering towards the tip of the scissors 65 which is rounded at a radius R' of about 0.01 mm to 0.03 mm.

FIG. 11A shows a third variation of the cutting device 50 with the tube-shaped probe 46 and the two cutting members disposed therein. In this variation the cutting blades 56 and 61 projecting from the probe 46 are configured approximately hook-shaped and are offset having a radius R relative to the longitudinal axis S—S and tapering towards the tip of the scissors 65. In the third variation, the length L extending from the front edge 46.2 of the probe 46 to the tip of the scissors 65 and the height H approximately 1.5 to 1.8 mm. The radius R is about 1.5 mm and the tip of the scissors 65 is arcuately bent relative to the longitudinal axis S—S at angle α at about 65°.

FIG. 11B shows the top view of the third variation of the cutting device 50 where the probe 46 is in retracted position relative to the cutting blades 56 and 61. Due to the spring-elastic restoring force, the two cutting blades 56 and 61 are spread apart from each other relative to the longitudinal axis. Differing from the first and second variation, in the third variation, pieces 53 and 66 are each integrally formed at the distal end of the cutting blades 56 and 61 and set-off in the direction of the longitudinal axis S—S. The sides of the two pieces 53 and 66 that are facing each other are each provided with cutting edges 57 respectively 62, that are ground onto the cutting blades.

The two pieces 53 and 66, which are associated with the cutting blades 56 and 61 are configured such that when moving the probe 46 in the direction of arrow X relative to the cutting members 55 and 60, the probe 46 slides along the longitudinally facing sides 54 and 64 of the two cutting blades 56 and 61, which are then compressed along the longitudinal axis S—S according to arrow Z in such a manner that the two cutting edges 57 and 62 are brought into a cutting engagement. The blade tip 58 and 63 of the pieces 53 and 66 have a round configuration with a radius R in the range of about 0.01 mm to 0.03 mm.

Figure 12A:
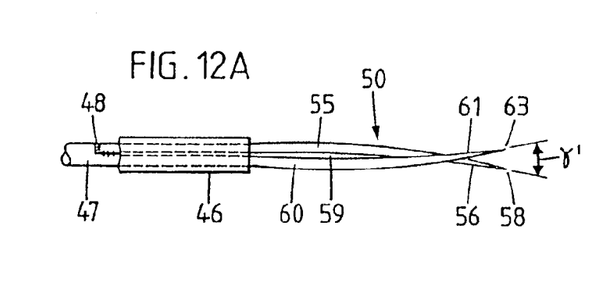
FIG. 12A is a side view of a fourth variation of the cutting device showing the two blade members in an approximate open position.
Figure 12B:
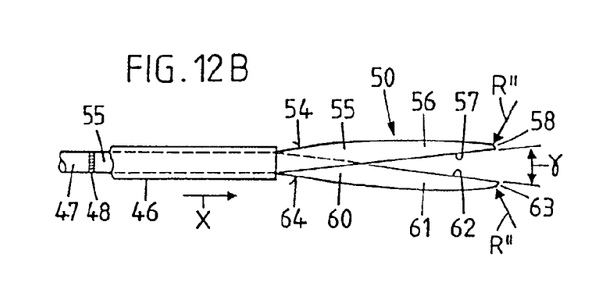
FIG. 12B is a top view of the cutting device according to FIG. 12A showing the two blade members.
Figure 12C:
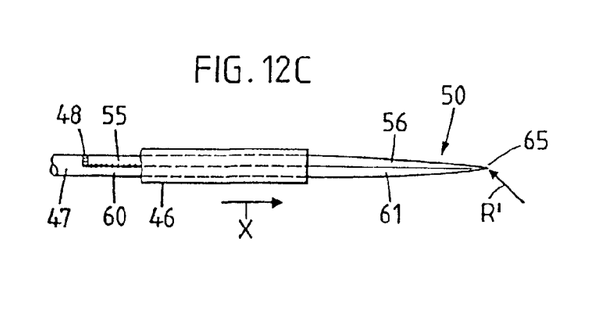
FIG. 12C is side view of the cutting device according to FIG. 12A showing the blade members in closed position.

In FIGS. 12A to 12C, a fourth variation of the cutting device 50 is shown on an enlarged scale with the tube-shaped probe 46 and supported therein the rod 47 with the two cutting members 55 and 60. In FIG. 12A the two cutting members 55 and 60 that are separated by a gap 59 are seen with the cutting blades 56, 61 integrally formed on the cutting members and with the blade tips 58, 63 in a substantially open position. In a different embodiment as that described in connection with FIGS. 9A, 10A and 11A, the cutting device 50 comprises, according to FIG. 12A, two cutting members 55 and 60 that have an elongated shape and are configured as axially straight members with cutting blades 56 and 61 integrally formed at the cutting members 55 and 61. In the position as shown in FIG. 12A, the two cutting blades 56, 61 are crossed relative to each other in the area of the cutting tips 58, 63 that are integrally formed at the cutting blades at an angle γ' in the range of about 1° to 3°, while in a preferred embodiment the angle γ' is 1.4°.

FIG. 12B shows a top view of the cutting device 50 according to FIG. 12A, with the two cutting members 55, 60 with their sliding- or lateral sides 54, 64 and the integrally formed cutting blades 56, 61 in a partly closed and in an approximate cutting position which is realized by the axial sliding motion of the probe 46. In the cutting position, the two cutting edges 57 and 62 of cutting blades 56, 61, starting from the two rounded blade tips 58 and 63 with a radius R'', are corresponding to each other at an acute opening angle γ. This configuration and dimension of each of the elements are described in the following paragraph in connection with the discussion of FIG. 14.

FIG. 12C is a side view of the fourth embodiment of the cutting device as shown in closed position realized through the axial sliding movement of the tube-shaped probe 46 in the direction of arrow X and with the two cutting blades 56, 61 tapering towards the round tip of the scissors 65.

Figure 13A:
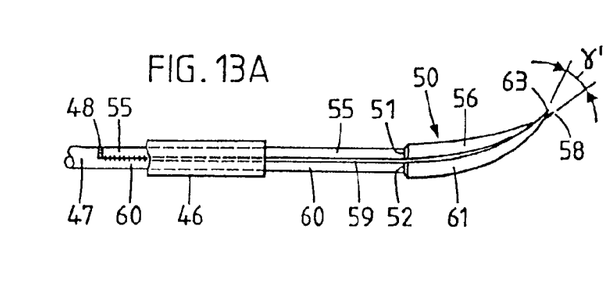
FIG. 13A is a side view of a fifth variation of the cutting device showing the blade members in open position.
Figure 13B:
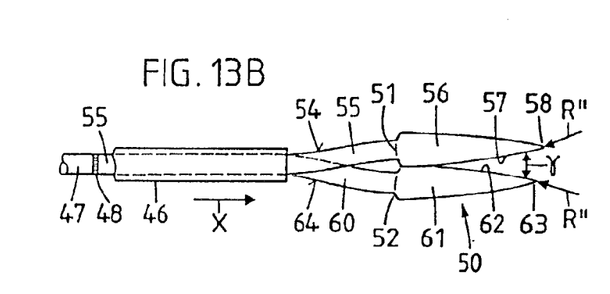
FIG. 13B is a top view of the cutting device according to FIG. 13A with the two blade members.
Figure 13C:
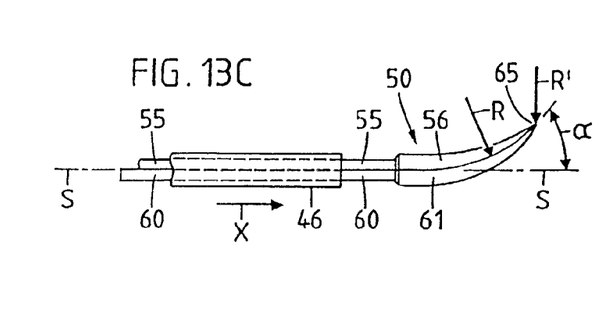
FIG. 13C is side view of the cutting device according to FIG. 13A with the blade members in closed position.

FIGS. 13A to 13C show a further embodiment of the cutting device 50 on an enlarged scale with the tube-shaped probe 46 and axially supported therein the rod 47 with the two cutting members 55, 63 and joined together at point 48. In FIG. 13A the two cutting members 55, 60 are separated by a gap 59, and provided with the blades 56, 61 integrally formed thereon, with the two blades tips 58, 63 in an open position. In the position as shown according to FIG. 13A, the two cutting blades 56, 61 with the integrally formed blade tips 58, 63 are crossed in the front portion at a crossing angle γ' which is in the range of about 1° to 3°, and in the preferred embodiment angle γ' is 1.4°.

In FIG. 13B, the cutting device 50 is shown in a top view according to FIG. 13A and the cutting members 55, 60 with the integrally formed cutting blades 56, 61 are in a closed position or, respectively in cutting position due to the axial sliding motion of the tube-shaped probe 46 in axial direction. The two cutting blades 56, 61 are disposed at the cutting members 55, 60, which are tapering in the direction starting from the crossing point 51 respectively crossing point 52 in the direction of the blade tip 58, respectively 63, and configured in the shape of a lance. The two cutting edges 57 and 62 that are facing each other correspond with each other at an acute opening angle γ starting from the rounded blade tips 58 and 63 each with a radius R".

FIG. 13C shows a side view the cutting device 50 according to FIG. 13A, where the two tapering cutting blades 56 and 61 are in closed position due to the axial sliding motion of the tube-shaped probe 46 in the direction of the round shaped blade tips. In the closed position, the two cutting blades 56, 61 form a relatively short cutting device 50, with the cutting blades 56, 61 at an acute offset angle α with the radius R relative to the longitudinal axis S—S and are likewise configured in arc-shape in the same direction. Each of the elements of the embodiments according to 13A to 13B have the same dimensions as the embodiment as, for example shown in FIGS. 9F or 10B.

The particular embodiment and dimensions of the distal end portion of the two cutting members 56, 61 and the afore-described cutting device generally referred to by reference number 50 is further described in the following paragraphs in connection with FIG. 14. FIG. 14 is a top view on an enlarged scale of the distal end of the cutting blades 56 and 61 of the respective cutting devices in an approximate cutting position. The two cutting edges 57 and 62 extend starting from the round blade tips 58 and 63 at a radius R" and correspond to each other at an acute opening angle γ along a distance D. The distance D is in the range of about 1.0 mm to about 2.0 mm and the opening angle γ is in the range of about 9° to 16°. In a preferred embodiment the distance D=1.5 mm and the opening angle γ'=12°. These dimensions provide a cutting action with a relatively short lift and exclusively in the outer angle range of the open cutting blades 56 and 61 or branches thereof The afore-described embodiments of the cutting device disposed at rod 47 and shown in the various Figures are interchangeably connected to the probe 46, for example such that the rod 47 is attached in the guide sleeve 45 by means of a threaded pin thereby forming a structural unit with the functional unit as shown in FIGS. 3 and 4.

While the invention has been illustrated and described as embodied in a micro surgical cutting instrument configured as scissors, it is not intended to be limited to the details shown since various modifications and structural changes may be made without departing in any way from the spirit of the present invention.

What is claimed as new and desired to be protected by Letters Patent is set forth in the appended claims:

What is claimed is:

1. A micro surgical cutting instrument configured as scissors comprising:
   an elongate housing formed as a handle having two housing parts having semi-circular cross sections which are spread apart against a spring pressure and in operative engagement with a sliding mechanism;
   a probe configured as a hollow needle and operatively connected to the sliding mechanism;
   a rod axially disposed in the hollow needle in form fitting engagement and secured in a control member of the sliding mechanism against axial displacement; wherein the probe is moved in axial direction by the control member of the sliding mechanism when the two housing parts are squeezed together;
   a cutting device disposed at a distal end of the rod and configured as scissors having two cutting members, each cutting member having one of an arcuate or straight configuration, each cutting member provided with a cutting blade and a cutting edge which, in an open position and extending from the distal end of the cutting blades towards a distal end of the probe, oppose each other at an acute angle such that when the probe is moved in axial direction towards a distal end of the cutting members, the cutting edges engage each other to establish a cutting action.

2. The microsurgical cutting instrument of claim 1, further comprising at least one light guide which is axially disposed within the tube-shaped probe; and wherein said light guide is connected at one end to a light source and at the other end is configured for illuminating a cutting action by the two cutting blades that correspond to each other in a closed or open position of the scissors.

3. The microsurgical instrument of claim 1, further comprising at least one optical guide supported axially within the probe and projecting from the distal end of the probe for optical recording of an immediate operating field and at the other end is connected to a camera and a corresponding monitor for projecting visual images of the optical recordation.

4. The microsurgical instrument of claim 1, wherein the at least two cutting blades projecting from the tube-shaped probe are jointly bent at a radius R relative to the longitudinal axis of the probe in the direction of a tip of the cutting blades at an acute bending angle α.

5. The microsurgical cutting instrument of claim 4, wherein a length of the two cutting blades starting from the front face of the probe and extending along the longitudinal axis to the tip of the cutting blades is not less than the height which extends from the outer diameter of the probe to the tip of the cutting blades.

6. The microsurgical instrument of claim 4, wherein a length of the two cutting blades starting from the front face of the probe and extending along the longitudinal axis to the tip of the cutting blades is less than the height which extends from the outer diameter of the probe to the tip of the cutting blades.

7. The microsurgical cutting instrument of claim 1, wherein each of the cutting blades disposed at the cutting members in the direction towards a tip of the cutting blade is configured as a straight cutting blade, and wherein in an open position of the cutting members, the two cutting edges starting from the tip of the cutting members in the direction of the probe correspond along a distance at an acute angle γ.

8. The microsurgical instrument of claim 1, wherein at a distance from the front face of the probe a cutting blade is disposed at each cutting member, each cutting member is configured in the shape of a lance and tapering in the direction toward a tip of the cutting member; and wherein the two cutting blades are jointly bent upwards relative to the longitudinal axis of the probe at an acute angle α and at a radius R.

9. The microsurgical instrument of claim 8, wherein the cutting edges which are disposed at the cutting blades are corresponding to each other at an open position of the cutting members starting from the tip of the cutting members in the direction of the probe along a distance D at an acute angle γ.

10. The microsurgical instrument of claim 1, wherein the two cutting blades disposed at the cutting members which are projecting from the probe are configured in the shape of an arcuate hook and are tapering in the direction of a tip of the scissors such that the blades corresponding with each other are brought into a cutting engagement at an inner side of each cutting blade by means of a piece when the probe is moved in axial direction.

11. The microsurgical instrument of claim 10, wherein a length of the hook shaped cutting blades extending from the front face of the probe along the longitudinal axis to the tip of the scissors with respect to the height extending from the arc-shaped outer edge of the cutting blades to the tip of the scissors is the same or larger.

12. The microsurgical instrument of claim 1, wherein the two cutting blades in a closed position and projecting from the probe are jointly bent relative to the longitudinal axis of the probe in the direction of a tip of the scissors at a bending angle a of about 40° to 60° and at a radius R of about 1.8 mm to 2.0 mm, and wherein a length extending form the front face of the probe to the tip of the scissors is about 2.5 mm to 3.8 mm and the height extending from the outer wall of the probe to the tip of the scissors is about 1.7 to 2.0 mm.

13. The microsurgical instrument of claim 1, wherein the two cutting blades in a closed position and projecting from the probe are jointly bent relative to the longitudinal axis of the probe in the direction of a tip of the scissors at a bending angle $\alpha$ of 60° and at a radius R of 2.0 mm, and wherein a length extending from the front face of the probe to the tip of the scissors is 3.0 mm and the height extending from the outer wall of the probe to the tip of the scissors is 1.55 mm.

14. The microsurgical instrument of claim 1, wherein the two cutting blades projecting from the probe are jointly bent directly at the front face of the probe relative to the longitudinal axis of the probe at a bending angle $\alpha$ of about 65° and a radius R of about 1.5 mm to 1.8 mm towards the tip of the scissors, and wherein the length extending from the front face of the probe to the tip of the scissors and the height extending from the outer wall of the probe to the tip of the scissors are in the range of 1.5 mm to 1.8 mm.

15. The microsurgical instrument of claim 1, wherein at an open position of the cutting members the distance extending from a tip of each of the cutting members in the direction of the probe is about 1.0 mm to 2.0 mm, preferably 1.5 mm and an opening angle $\gamma$ is about 9° to 16°, preferably 12°.

16. The microsurgical instrument of claim 1, wherein the two cutting blades with integrally formed blade tips are crossed in an open position corresponding to each other at a crossing angle $\gamma'$ of about 1° to 3°, preferably 1.4°.

17. The microsurgical instrument of claim 1, wherein in a closed position of the scissors the two cutting blades with integrally formed blade tips jointly form a round tip of the scissors with a radius R' in the range from 0.01 mm to 0.03 mm.

18. Use of the microsurgical instrument of claim 17 as an ophthalmologic scissors for the insertion into the vitreous humor of an eye and the treatment of retinal diseases.

19. The microsurgical instrument of claim 1, further comprising:
   a light guide which is connected at one end to a light source and which is axially supported in the probe is associated at a distance with the two cutting members; and
   wherein the light guide is configured for illuminating the two cutting blades that are configured upwardly bent or straight when the scissors are at an open position or at a closed position; and
   an optical guide co-axially supported in an optical channel extending co-axially in the probe; and
   wherein the optical channel supporting the optical guide is configured at a distal end for optical recordation of the surgical procedure; and
   wherein another end of the optical channel supporting the optical guide is connected to a camera, which is connected to a monitor screen for visually presenting images from the surgical field.

20. Use of the microsurgical instrument of claim 1 as an ophthalmologic scissors, particularly for insertion into the vitreous humor of an eye and the treatment of retinal diseases.

21. Use of the microsurgical instrument of claim 1 as a surgical scissors for the insertion into the body cavities of a living being for carrying out surgery.

22. Use of the microsurgical instrument of claim 1 as a surgical scissors for the insertion into the body cavities of a living being for carrying out surgery.

23. In a method of ophthalmologic microsurgery and for the treatment of retinal surgery the improvement which comprises use of the microsurgical instrument of claim 1 as ophthalmologic scissors for insertion into the vitreous humor of an eye and to conduct retinal surgery.

24. In a method of surgery the improvement which comprises use of the microsurgical instrument of claim 1 as a surgical scissors for the insertion into the body cavities of a living being.

\* \* \* \* \*